United States Patent
Muncie

(10) Patent No.: US 6,673,078 B1
(45) Date of Patent: Jan. 6, 2004

(54) SURGICAL WIRE AND PIN EXTRACTOR

(76) Inventor: Robert H. Muncie, 22 Smartestate Rd. P.O. Box 13, Lee, ME (US) 04455-0013

( * ) Notice: Subject to any disclaimer, the term of this patent is extended or adjusted under 35 U.S.C. 154(b) by 0 days.

(21) Appl. No.: 10/200,748

(22) Filed: Jul. 24, 2002

(51) Int. Cl.[7] ............................................. A61B 17/28
(52) U.S. Cl. ..................... 606/104; 606/205; 606/206
(58) Field of Search ..................... 686/104, 205–208, 686/210, 211, 151

(56) References Cited

U.S. PATENT DOCUMENTS

| | | | | |
|---|---|---|---|---|
| 430,849 A | * | 6/1890 | Groth | 606/206 |
| 1,274,669 A | * | 8/1918 | Bohn | 606/206 |
| 4,472,141 A | * | 9/1984 | Dragan | 604/232 |
| 5,281,230 A | * | 1/1994 | Heidmueller | 606/127 |
| 5,304,183 A | * | 4/1994 | Gourlay et al. | 606/142 |
| 5,308,357 A | * | 5/1994 | Lichtman | 606/205 |
| 5,318,589 A | * | 6/1994 | Lichtman | 606/205 |
| 5,486,185 A | * | 1/1996 | Freitas et al. | 606/142 |
| 5,645,075 A | * | 7/1997 | Palmer et al. | 606/205 |
| 5,665,100 A | * | 9/1997 | Yoon | 606/170 |
| 6,090,129 A | * | 7/2000 | Ouchi | 606/206 |
| 6,123,678 A | * | 9/2000 | Palmer et al. | 606/205 |
| 6,361,540 B1 | * | 3/2002 | Gauderer et al. | 606/106 |

* cited by examiner

Primary Examiner—Michael J. Milano
Assistant Examiner—Jessica R Baxter
(74) Attorney, Agent, or Firm—Marks & Clerk

(57) ABSTRACT

The medical instrument disclosed includes a pair of jaws which are clamped to an end of a surgical wire or pin. The jaws are pressed together, not by the usual Jacobs' chuck arrangement, but by the operation of a cam lever. The lever is mounted in the hand-grip of the instrument. This arrangement makes it possible for the wire or pin to be gripped with a large force, yet to be gripped delicately and precisely so that damage to the surrounding tissue is kept to a minimum. The instrument is T-shaped as to its general shape, and the cam lever operates the jaws by means of a collet action by which a jaw member is axially moved within the hollow stem of the T. The inside end of the stem and a portion of the outer end of the jaw member forming a pair of opposed camming surfaces.

14 Claims, 3 Drawing Sheets

SURGICAL WIRE AND PIN EXTRACTOR

FIELD OF THE INVENTION

This invention relates to surgical instruments for use in conjunction with bone fixation components such as pins and wires, and more particularly relates to instruments for the removal of such components.

1. Background of the Invention

It is quite common, when carrying out surgical procedures on bones, particularly in the hands, and also generally in the limbs, to implant a pin or wire into the injured or diseased bone. The purpose of the wire is to reinforce the bone during healing. Particularly in surgery of the hand, where wire is used, an end of the wire may be left protruding from the skin to make it easy to remove the wire later, or the wire may be trimmed below the level of the skin.

2. Description of the Prior Art

Instruments are available for extracting surgical wires and pins. Some such instruments are based on the principle of using a Jacobs' chuck to tighten the instruments onto the wire, whereupon the wire can be drawn clear of the bone, and discarded. Other instruments are merely special forms of pliers adapted for a particular medical situation.

A problem that arises with most known instruments is that the tissues around the area from which the wire is extracted can become severely traumatised by the manipulation of the wire; and by the manipulation of the extractor so as to attach it to the wire. The reason is that the known instruments have been too heavy and cumbersome and awkward. It has proved to be too difficult for a surgeon to consistently tighten a chuck, using a chuck key, onto the wire with the degree of sensitivity and delicacy that is required to avoid damaging the surounding tissues.

An instrument that is somewhat lighter and easier to use than a typical Jacobs' chuck is disclosed in U.S. Pat. No. 4,263,903. It comprises a one piece jaw that is contained in a slender body means. In order to close the jaws, it relies on the body means to act on a cam surface located on the outer surfaces of the jaws. As the jaws are pulled up into the body means, they are forced together. The jaws are pulled into the body means by rotating a screw thread assembly. This method of bringing the jaws together takes a longer period of time than is desirable and also requires a great deal of hand movement. It could therefore, cause necessary trauma and tissue damage.

SUMMARY OF THE INVENTION

In accordance with one aspect of the present invention, there is provided an instrument for extracting surgical wires, particularly surgical wires such as K-wire™. Surgical wires include such things as wires, pins, staples, and intramedullary nails. The instrument will permit the user to consistently tighten a portion of the instrument onto the wire with the appropriate delicacy. The present invention provides an instrument that can be tightened and otherwise manipulated by the user with the delicacy expected for work of this nature. This is in part due to the tactile feedback experienced by the user. This tactile feedback is a result of the reaction forces generated by the gripping of the pin or wire. These forces are transmitted, at least in part, back to the user's hand.

In the present invention, the instrument may be operated by a single hand. It is provided with a hand-grip, a cam lever, a pair of jaws, and a collet. The cam lever is operable by the hand while holding the hand-grip. The cam lever draws the jaws, which grip the surgical wire or pin, up into the collet. A tapered surface on the collet acts on the cam surface of the jaws to urge the jaws together. The action of closing the hand is sufficient to perform this action, thus making the gripping action very quick, which is effective in reducing trauma and tissue damage.

It has been found, by this invention, that the combination of the cam lever and the camming action between the jaws and the collet makes it possible to apply a strong gripping force to the jaws in a very controlled manner. The undesired side-forces that could hardly be avoided with the Jacobs' chuck, are virtually non-existent with this invention. It is these uncontrolled side-forces particularly that typically lead to trauma and tissue damage.

It has also been found to be beneficial that there are only two opposed jaw surfaces, rather than the three wedge-shaped jaw pieces usual to a Jacobs' chuck.

There is some friction associated with both the tapered collet and cam surface mechanism and the sliding and rubbing cam lever mechanism. It is recognized in the present invention that some friction here is beneficial, since it may be desirable that the gripping force be partially locked in even if the grip on the cam lever should be relaxed. If there were to be a frictionless connection between the jaws and the cam lever, then the grip of the jaws would relax as the force on the cam lever was relaxed.

On the other hand, the friction should not be so great that the magnitude of the jaw gripping force is unduly diminished. It has been found, in the present invention, that the combination of the tapered collet and cam mechanism and the cam lever mechanism gives a suitable degree of friction.

In this invention, the cam lever is operated by the hand that grips the hand-grip. This frees the other hand for the purpose of steadying the instrument, or otherwise manipulating the patient's body or surgical site using the surgeon's own hand-eye co-ordination without the need for voice commands to a nurse or other surgical assistant—or indeed, to the patient. This, again, reduces the likelihood of generating side-forces, which would result in trauma or tissue damage.

Additionally, a squeeze grip type of action is one of the easiest ways of applying a large force in a well controlled manner. This is due to the relatively high gripping strength of a human hand and to the fact that the gripping forces are applied roughly co-linearly to the direction of application of gross force during the removal of the surgical wire.

The strength of the grip needed from the instrument, to pull the wire or pin out, can be quite large. Thus, the jaw must be robust enough to withstand a heavy twisting action, because it may be necessary to rotate the instrument to make it easier to extract the wire or pin. The collet and cam combination of the present invention permits construction of an instrument having jaws of sufficient size, and of suitable material, that can easily cope with the noted forces, without undue distortion. In the present invention, all the components of the instruments, though simple to construct, can be sturdy and reliable over a long service life, with none of the components being subject to undue wear.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following discussion.

Figure 1:
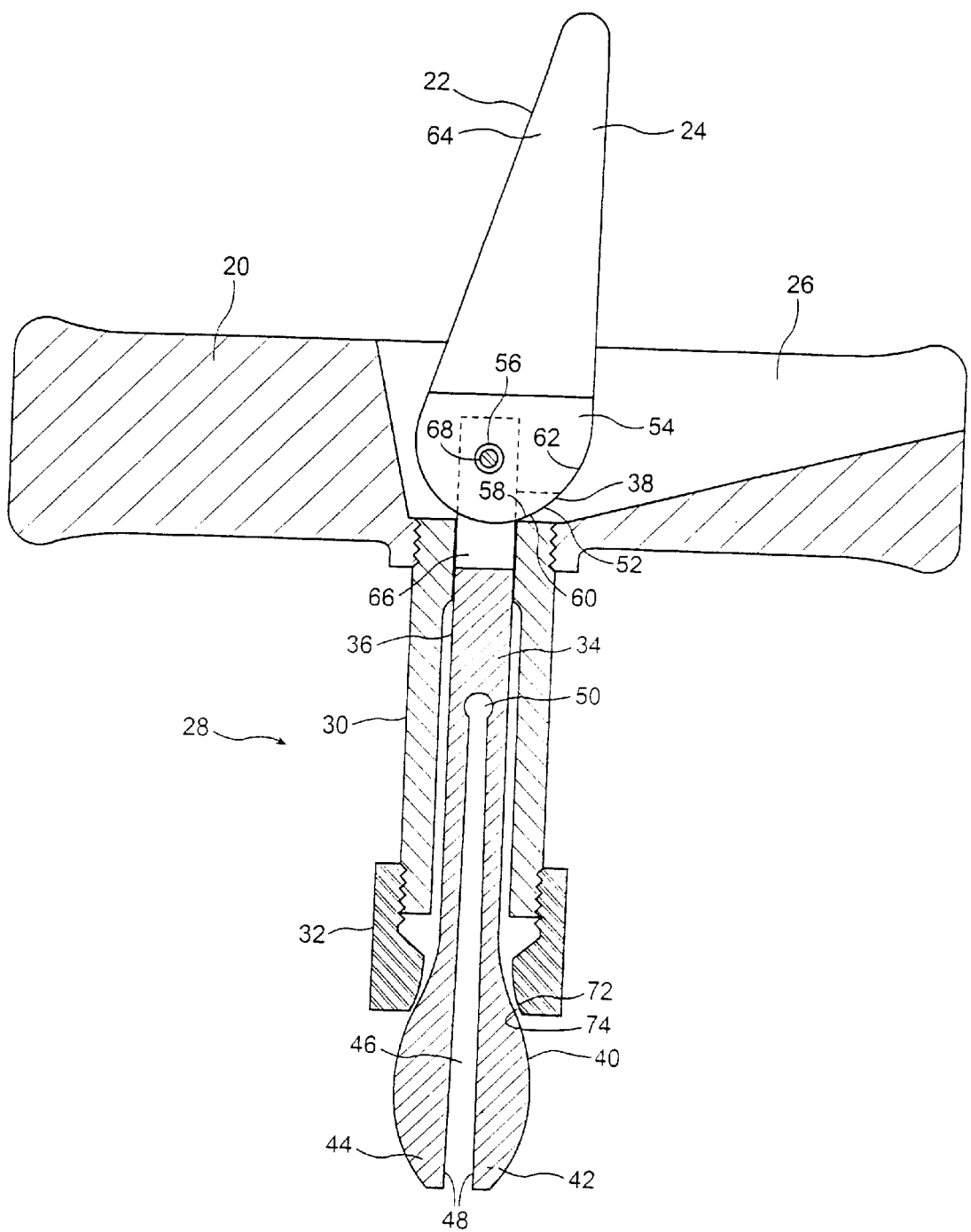
FIG. 1 is a partial cross-section of an instrument that embodies this invention.

The instrument illustrated is generally T-shaped, as can be seen in FIG. 1. It is sized to be easily gripped in the hand, with the fingers and thumb wrapped around the hand-grip 20. The palm of the hand is generally in intimate contact with the top surface 22 of a cam lever 24. The hand-grip 20 includes a slot 26 for receiving the cam lever 24.

Depending from the bottom of the hand-grip 20 is a stem member 28. The hand-grip 20 and the stem member 28 are joined together in a threadible relation in order to permit relative adjustment of these two parts. Such adjustment may become necessary as the instrument becomes worn through use. This method of adjoinment also allows the stem to be replaced if necessary, or for alternate stems to be used.

The stem member 28 comprises a hollow stem portion 30 and a sleeve means 32, which is typically a collet. Hollow stem portion 30 and sleeve means 32 are preferably adjoined in threadible relation.

The stem member 28 contains a jaw member 34 which is arranged for axial movement within the hollow interior 36 thereof. The jaw member 34 comprises a proximal end 38 and a distal end 40. The distal end 40 comprises a pair of opposed jaws 42 and 44. These opposed jaws 42 and 44 are defined by a slit 46 in jaw member 34. Jaws 42 and 44 therefore comprise the material of the jaw member 34 at the sides of the slit 46. The width of the slit 46 can be controlled by changing the length of stem member 28. This is accomplished by adjusting sleeve means 32 until the desired size of the slit is obtained. The inner sides of jaws 42 and 44 form substantially planar opposing surfaces 48 to be used for gripping surgical wire, pins, and the like.

As will be observed from the illustrations, when the jaw member 34 is moved upwardly, the jaws 42 and 44 are squeezed together by a camming or wedging action. Together, jaws 42 and 44 and sleeve means 32 form a gripping means.

The slit 46 extends a substantial distance up the length of the jaw member 34, such that the jaws 42 and 44 are of sufficient length so as to be fairly readily elastically deformed. The slit 46 has an enlarged end 50 to dissipate any stresses that may have been caused by cutting or otherwise forming the slit 46 into the material of the jaw member 34. The slit can also be used to accommodate a portion of the length of the wire or pin that has been pulled out of the patient. This allows the instrument to be easily repositioned closer to the point at which the wire or pin exits the tissue.

It is necessary when removing a pin or wire, to grip the pin or wire with substantial force. The gripping force typically generated by a human hand is insufficient for holding onto a pin or wire for the purpose of removal by pulling. In order to generate the amount of force necessary, some sort of mechanical means must be used to multiply the forces generated by the hand. The present invention uses a double camming action in order to gain the necessary mechanical advantage for producing sufficient gripping strength.

Figure 2:
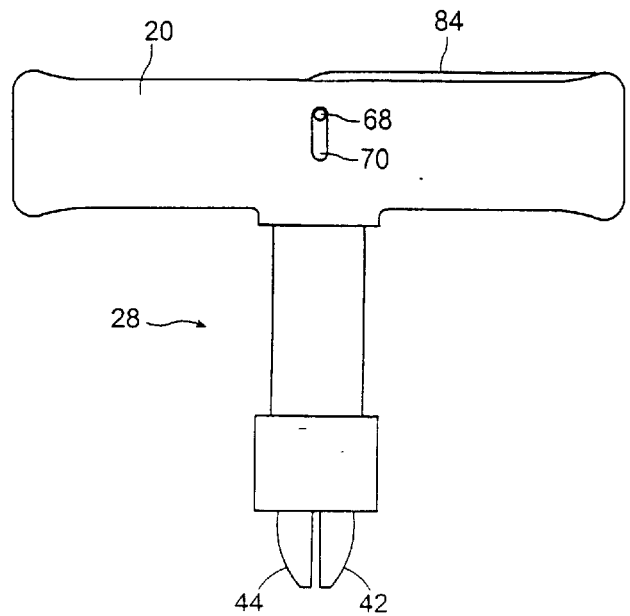
FIG. 2 is a view corresponding to that of FIG. 1, showing the instrument at a different stage of use.

The first camming action is produced by a lever means in form of a cam lever 24 located at the top of the instrument. The cam lever 24 includes a cam surface 52 which comprises a plurality of radii that are preferably substantially concentric. The cam surface 52 is actually formed on a tongue portion 54 of cam lever 24. Included in the tongue portion 54 is a substantially circular aperture 56, which is preferably located centrally to the radii of cam surface 52. When the cam lever 24 is in position shown in FIG. 1, a first portion 58 of the cam surface 52 engages a cam reaction surface 60 at the top of the stem member 28. When the cam lever 24 is in the position shown in FIG. 2, a second portion 62 of the cam surface 52 engages the cam reaction surface 60 of the stem 28. The respective radii of the first and second portions of 58 and 62 respectively of the cam surface 52 are different, with the radius at first portion 58 being lesser and the radius at second portion 62 being greater. As the cam lever 24 is rotated from the position shown in FIG. 1 to the position shown in FIG. 2, the aperture is displaced to a greater distance from the reaction surface 60. The distance along the cam lever 24 from the aperture 56 to the area 64, where hand grip forces are applied, is a plurality of times greater than the largest radius of the cam, thus providing the required mechanical advantage.

The proximal end 38 of the jaw member 34 includes a slot 66 for receiving tongue portion 54 of cam lever 24. Jaw member 34 is pivotally connected to the cam lever 24 through pin 68, which is adapted to fit snugly into aperture 56 of the cam lever.

The axial movement of the jaw member 34 within the stem member 28 is controlled through the use of cam lever 24. As the cam lever is rotated, the pivot pin 68 is moved along guide slot 70, from the position shown in FIG. 1 to the position shown in FIG. 2. The force on the pin is in turn transmitted to the jaw member 34. This force pulls the jaw member 34 into the hollow interior 36 of the stem member 28 which in turn initiates the second camming action, thereby causing a change in the relative opening of jaws 42 and 44.

The second camming action occurs at the distal end of the stem member 28. The sleeve means 32 contained thereon is thereby provided with a female camming surface 72. The jaw member 34 is provided with a male curved camming surface 74. When the cam lever 24 is in an upwardly oriented position, as in FIG. 1, the camming surfaces 72 and 74 are disengaged and the jaws 42 and 44 are therefore spread apart. As the jaw member 34 is pulled into the stem member 28, the male curved camming surface 74 contacts the female camming surface 72 thereby transmitting the pulling force to jaws 42 and 44. When the cam lever 24 is in a downwardly oriented position, as in FIG. 2, the jaws 42 and 44 have moved together sufficiently to grip a surgical wire or pin that is to be extracted.

The male curved camming surface 74 is shaped so as to provide a more severe camming action as the jaws 42 and 44 first contact the stem member 28, and to provide less severe camming action after the jaws 42 and 44 have entered at least part way into the stem. This non-linear camming configuration accommodates the increased resistance to the pulling of the jaw member 34 due to increased friction caused by the outwardly exerted force of the jaws 42 and 44.

In order to improve the grip of the jaws 42 and 44 onto the surgical wire being extracted, the opposing surfaces 48 may be modified so as to have enhanced gripping characteristics. Typically, diamond dust may be adhered to or otherwise cemented to the opposing surfaces 48; or alternatively, the opposing surfaces 48 may be machined in such a manner as to create a frictional or serrated surface on each.

Figure 3:
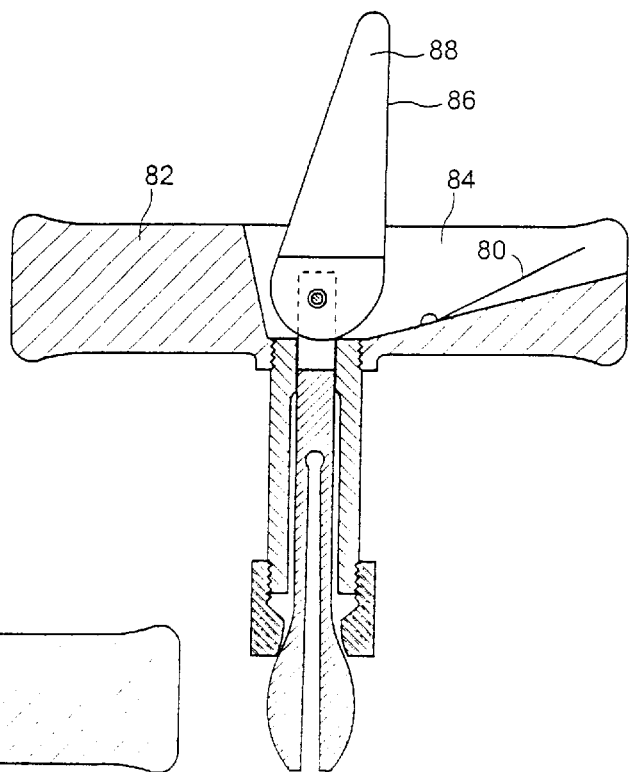
FIG. 3 is a view similar to FIG. 1, showing an alternative embodiment of the invention.

An alternative embodiment of the invention is disclosed in FIG. 3 which shows a spring member 80 securely fastened to hand-grip 82, and preferably located in the slot 84. The spring member acts against the undersurface 86 of cam lever 88 thus providing a resistive force as the handle is pressed down. The main purpose of the spring is to provide an unlocking force to assist in moving cam lever in an upward direction. The friction between the jaw member 90 and the stem member 92 resists the lever from moving upwardly.

Figure 4:
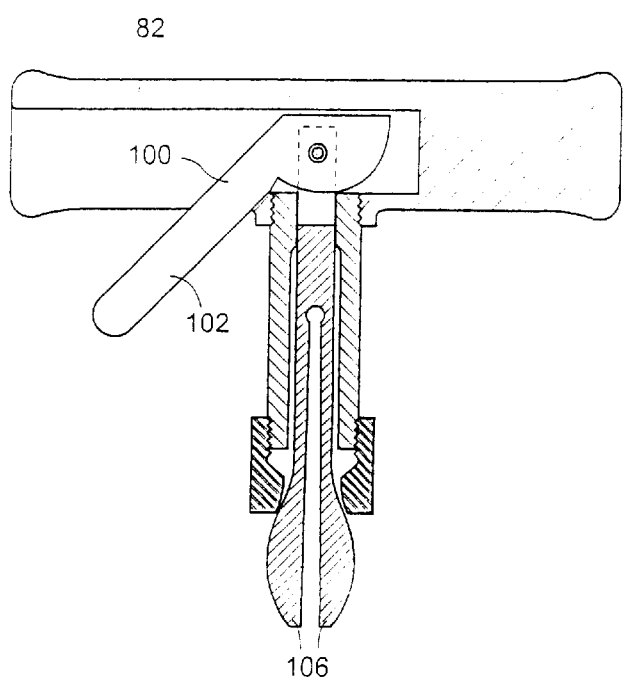
FIG. 4 is a view similar to FIG. 1, showing an alternative embodiment of the invention that incorporates a different cam lever configuration.

Another alternative embodiment of the invention is disclosed in FIG. 4 which shows a downwardly extending cam lever configuration. The cam lever 100 includes a gripping portion 102 that extends from the bottom of the hand-grip 104, and is therefore in intimate contact with the fingers rather than the palm of the hand. The forces are transmitted from the cam lever 100 to the jaws 106 in a manner analogous to the embodiment of FIG. 1.

Figure 5:
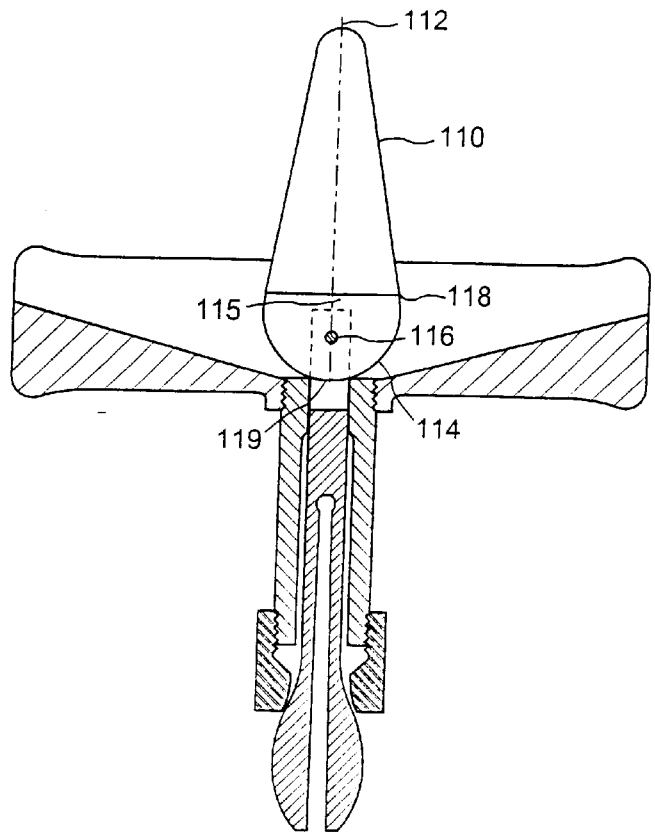
FIG. 5 is a view similar to FIG. 1, showing an alternative embodiment of the invention that incorporates a different type of cam.

Another alternative embodiment of the invention is disclosed in FIG. 5 which shows a cam lever configuration that is operable bi-directionally. The cam lever 110 is symmetrical about its centre line 112 and the cam surface 114 is of a constant radius, with the centre 115 of the radius substantially on the centre line 112. The aperture 116 in the tongue portion 118 of the cam lever 110, is also substantially on the centre line 112, but is offset from the centre 115 of the radius toward the cam surface end 119 of the cam lever. The camming action is produced as a result of this offset. It is readily apparent that the similar camming action would be produced by rotating the cam lever in either direction.

Figure 6:
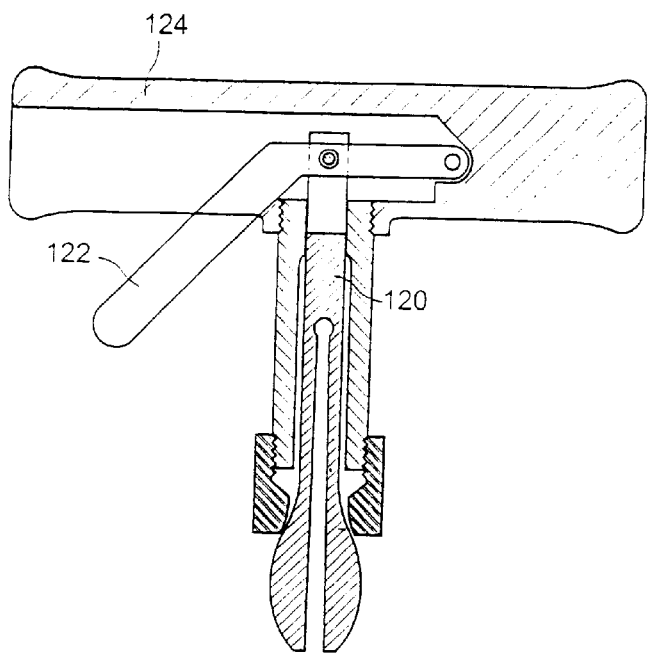
FIG. 6 is a view similar to FIG. 1, showing an alternative embodiment of the invention that incorporates a different type of lever arm system.

A further alternative embodiment of the invention is disclosed in FIG. 6, which shows a simple first order lever system that is used to lift the jaw member 120 when the lever arm 122 is moved toward the handle-grip 124.

A still further embodiment, not shown in the figures, includes a cam surface that has a maximum radius between the two ends of the cam surface, and thus incorporates an over-the-centre action as the cam lever is rotated. This feature serves to lock the lever in place, thus freeing the user's gripping hand while maintaining the gripping force on the pin or wire.

In addition to the instrument herein described being used to remove surgical pins and wires, it is possible to use the instrument for insertion of surgical pins and wires. It may be necessary, however, to use additional apparatus in conjunction with the instrument when used as an insertion device.

Furthermore, this instrument could also be adapted for use in conjunction with other surgical bone fixation means such as staples, intramedullary nails, or drills. Such adaptation could require the jaws to be of a particular configuration for each specific use.

Other modifications and alterations may be used in the design and manufacture of the surgical wire and pin puller of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element.

What is claimed is:

1. A hand operated medical instrument for the purpose of gripping surgical wires, comprising:

gripping means, having a pair of closable jaws with generally opposed gripping surfaces, with said jaws being adapted to grip surgical wire, and sleeve means for producing a camming action between said sleeve means and said jaws when relative axial movement takes place therebetween, thereby causing a change in the relative opening of said jaws;

a hand-grip grippable in use by one hand of the user;

lever means associated with said hand-grip, having a portion of said lever means spaced from said hand grip for displacement by said one hand of the user when in use; and connecting means between said gripping means and said lever means wherein the relative displacement of said connecting means, caused by a corresponding displacement of said lever means relative to said hand grip, moves said jaws and said sleeve means axially with respect to one another;

wherein said sleeve means is a collet threadably engaged on a stem member and disposed at the end thereof opposite to said hand-grip;

wherein said jaws include a male camming surface, and said collet includes a female camming surface, with said male and female camming surfaces being complementary; and wherein said lever provides a mechanical advantage whereby the force transmitted to the connecting means in is greater than the force used to displace said lever means, and wherein said displacement of said lever means relative to said hand grip is greater than said relative displacement of said connecting means.

2. The hand operated medical instrument of claim 1, wherein the resulting instrument is generally T-shaped.

3. The hand operated medical instrument of claim 1, wherein said pair of closable jaws and said connecting means form an integral jaw member, said jaw member having a slit which defines said relative opening of said jaws.

4. The hand operated medical instrument of claim 3, wherein said jaw member has a proximal end and a distal end, with said proximal end disposed toward said hand-grip and said distal end disposed downwardly therefrom.

5. The hand operated medical instrument of claim 4, wherein said distal end forms said pair of closable jaws.

6. The hand operated medical instrument of claim 1, wherein said connecting means and said closable jaws form an integral jaw member, and wherein said integral jaw member is substantially contained within said stem member.

7. The hand operated medical instrument of claim 1, wherein said male camming surface is shaped so as to provide a progressively less severe camming action as the spaced relation of the jaws becomes narrower.

8. The hand operated medical instrument of claim 1, wherein said lever means is a cam lever with a cam surface located along one end thereof.

9. The hand operated medical instrument of claim 8, wherein said cam surface is composed of a plurality of generally concentric radii wherein said cam surface is in contact with a complementary cam reaction surface which is disposed near the proximal end of said connecting means.

10. The hand operated medical instrument of claim 1, wherein said lever means is on a pivot.

11. The hand operated medical instrument of claim 10, wherein said connecting means and said lever means are held in relative rotatable relation.

12. The hand operated medical instrument of claim 8, wherein said cam surface is a constant radius and pivots at a point offset to the centre of said radius.

13. The hand operated medical instrument of claim 1, wherein said stem member and said hand-grip are threadably and adjustably engaged.

14. A hand operated medical instrument for the purpose of gripping surgical wires, comprising:

gripping means, having a plurality of closable jaws with generally opposed gripping surfaces, with said jaws being adapted to grip surgical wire, and sleeve means for producing a camming action between said sleeve means and said jaws when relative axial movement takes place therebetween, thereby causing a change in the relative opening of said jaws;

a hand-grip grippable in use by one hand of the user;

lever means associated with said hand-grip, having a portion of said lever means spaced from said hand grip for displacement by said one hand of the user when in use; and connecting means between said gripping means and said lever means wherein the relative displacement of said connecting means, caused by a corresponding displacement of said lever means relative to said hand grip, moves said jaws and said sleeve means axially with respect to one another;

wherein said sleeve means is a collet threadably engaged on a stem member and disposed at the end thereof opposite to said hand-grip;

wherein said lever provides a mechanical advantage whereby the force transmitted to the connecting means in is greater than the force used to displace said lever means, and wherein said displacement of said lever means relative to said hand grip is greater than said relative displacement of said connecting means.

* * * * *